United States Patent
Chen et al.

(10) Patent No.: US 10,696,619 B2
(45) Date of Patent: Jun. 30, 2020

(54) METHOD FOR PREPARING DIALKYL CARBONATE

(71) Applicant: INDUSTRIAL TECHNOLOGY RESEARCH INSTITUTE, Hsinchu (TW)

(72) Inventors: Yen-Chih Chen, Changhua (TW); Man-Yin Lo, Zhubei (TW); Hsi-Yen Hsu, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 16/232,902

(22) Filed: Dec. 26, 2018

(65) Prior Publication Data

US 2019/0202770 A1 Jul. 4, 2019

(30) Foreign Application Priority Data

Dec. 28, 2017 (TW) .............................. 106146231 A

(51) Int. Cl.
*C07C 68/04* (2006.01)
*B01J 21/06* (2006.01)
*B01J 23/10* (2006.01)

(52) U.S. Cl.
CPC ............. *C07C 68/04* (2013.01); *B01J 21/066* (2013.01); *B01J 23/10* (2013.01)

(58) Field of Classification Search
CPC ................................ C07C 68/04; B01J 21/066
See application file for complete search history.

(56) References Cited

U.S. PATENT DOCUMENTS

| | | | |
|---|---|---|---|
| 8,629,295 B2 * | 1/2014 | Koh ................. | C07C 68/00 558/277 |
| 8,663,564 B2 | 3/2014 | Nowlan et al. | |
| 8,809,569 B2 | 8/2014 | Zhang et al. | |
| 9,334,228 B2 * | 5/2016 | Baik ................. | C07C 68/00 |
| 9,371,269 B2 * | 6/2016 | Koh ................. | C07C 68/00 |
| 9,656,943 B2 | 5/2017 | Huang et al. | |
| 2011/0196167 A1 | 8/2011 | Almusaiteer et al. | |
| 2011/0288309 A1 | 11/2011 | Nowlan et al. | |

FOREIGN PATENT DOCUMENTS

| | | | |
|---|---|---|---|
| CN | 101143322 A | 3/2008 | |
| CN | 101632932 B | 12/2012 | |
| CN | 101947425 B | 5/2013 | |
| CN | 102423707 B | 5/2014 | |
| CN | 102659601 B | 6/2014 | |
| CN | 103044491 B | 5/2015 | |
| CN | 104841414 A | 8/2015 | |
| JP | 2009-242306 A | 10/2009 | |
| JP | 2010-77113 A | 4/2010 | |
| JP | 2011-51904 A | 3/2011 | |
| JP | 2012-162623 A | 8/2012 | |
| JP | 6184048 B2 | 8/2017 | |
| TW | 200400176 A | 1/2004 | |
| TW | 201531460 A | 8/2015 | |
| TW | I593676 B | 8/2017 | |
| WO | WO 2013/175510 A1 | 11/2013 | |
| WO | WO 2014/070415 A1 | 5/2014 | |

OTHER PUBLICATIONS

Aresta et al., "Cerium(IV)oxide modification by inclusion of a hetero-atom: A strategy for producing efficient and robust nano-catalysts for methanol carboxylation", Catalysis Today, vol. 137, 2008, pp. 125-131.
Honda et al., "Organic carbonate synthesis from CO2 and alcohol over CeO2 with 2-cyanopyridine: Scope and mechanistic studies", Journal of Catalysis, vol. 318, 2014 (available online Aug. 17, 2014), pp. 95-107.
Taiwanese Office Action and Search Report, dated Sep. 7, 2018, for Taiwanese Application No. 106146231.
Tomishige et al., "A novel method of direct synthesis of dimethyl carbonate from methanol and carbon dioxide catalyzed by zirconia", Catalysis Letters, vol. 58, 1999, pp. 225-229.
Tomishige et al., "Catalytic and direct synthesis of dimethyl carbonate starting from carbon dioxide using CeO2—ZrO2 solid solution heterogeneous catalyst: effect of H2O removal from the reaction system", Applied Catalysis A: General, vol. 237, 2002, pp. 103-109.
Zhang et al., "Cerium oxide-based catalysts made by template-precipitation for the dimethyl carbonate synthesis from Carbon dioxide and methanol", Journal of Cleaner Production, vol. 103, 2015 (available online Sep. 16, 2014), pp. 847-853.

* cited by examiner

*Primary Examiner* — Golam M Shameem
(74) *Attorney, Agent, or Firm* — Birch, Stewart, Kolasch & Birch, LLP

(57) ABSTRACT

A method for preparing dialkyl carbonate is provided. The preparation method includes the following steps. An alcohol compound, carbon dioxide and a catalyst are mixed to form a mixing solution. Organic acid is added to the mixing solution to carry out a synthesis reaction of dialkyl carbonate. The alcohol compound includes methanol, ethanol, propanol or butanol. The catalyst includes cerium oxide, zirconium oxide, titanium oxide, lanthanum oxide or a combination thereof. The organic acid includes formic acid, acetic acid, propionic acid, butyric acid, valeric acid or a combination thereof.

11 Claims, No Drawings

METHOD FOR PREPARING DIALKYL CARBONATE

CROSS REFERENCE TO RELATED APPLICATIONS

This Application claims priority of Taiwan Patent Application No. 106146231, filed on Dec. 28, 2017, the entirety of which is incorporated by reference herein.

TECHNICAL FIELD

The disclosure relates to a method for preparing dialkyl carbonate, and relates to a method for preparing dialkyl carbonate which includes adding with organic acid in a synthesis reaction.

BACKGROUND

Dimethyl carbonate (DMC) is one of the most important derivatives of carbon dioxide. It is a new type of green chemical raw material, which can be widely used in solvents, gasoline additives, lithium-ion battery electrolytes, etc. Global demand exceeds 500,000 tons and the output value has reached US$391M. DMC is also a precursor of many high value-added chemicals such as PC, ADC, MDI, TMAH, TMD, etc. However, high-stability carbon dioxide causes the overall reaction rate to be slow, requiring high-performance catalysts to reduce the activation energy of the reaction. The heterogeneous catalytic reaction is a three-phase reaction of carbon dioxide (gaseous), alcohol (liquid) and catalyst (solid). Carbon dioxide and alcohol must be simultaneously adsorbed on the surface of the catalyst for the reaction to proceed. At present, the main catalysts are mostly cerium oxide ($CeO_2$), zirconium oxide ($ZrO_2$) or a mixture thereof. Although they have catalytic activity, their efficiency is not high. Therefore, it is necessary to develop a new process to improve the reaction efficiency of the catalyst.

Currently, most of the improvement of the catalyst is made by using a metal additive and sintering together with the catalyst. However, since the synthesis reaction of DMC is a three-phase reaction and the catalyst is solid, the additive itself, due to the problem of dispersion, leads to limited effectiveness.

SUMMARY

In accordance with one embodiment of the disclosure, a method for preparing dialkyl carbonate is provided. The preparation method includes the following steps. An alcohol compound, carbon dioxide and a catalyst are mixed to form a mixing solution. Organic acid is added to the mixing solution to carry out a synthesis reaction of dialkyl carbonate.

A detailed description is given in the following embodiments.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

In accordance with one embodiment of the disclosure, a method for preparing dialkyl carbonate is provided. The preparation method includes the following steps. An alcohol compound, carbon dioxide and a catalyst are mixed to form a mixing solution. Organic acid is added to the mixing solution to carry out a synthesis reaction of dialkyl carbonate.

In some embodiments, the alcohol compound may include methanol, ethanol, propanol or butanol.

In some embodiments, the catalyst may include, for example, cerium oxide ($CeO_2$), zirconium oxide ($ZrO_2$), titanium oxide ($TiO_2$), lanthanum oxide ($La_2O_3$) or a combination thereof.

In some embodiments, the organic acid may include formic acid, acetic acid, propionic acid, butyric acid, valeric acid or a combination thereof.

In some embodiments, the catalyst is in an amount of about 0.5-25 parts by weight, based on 100 parts by weight of the alcohol compound.

In some embodiments, the organic acid is in an amount of about 0.01-2 parts by weight, based on 100 parts by weight of the alcohol compound. If the amount of organic acid is too low or too high, the reactivity will decrease.

In some embodiments, the preparation method further includes adding a dehydrating agent to the mixing solution.

In some embodiments, the dehydrating agent may include 2-cyanopyridine, alkali metal silicoaluminate (zeolite molecular sieves, such as 3A zeolite molecular sieves), benzonitrile, 2,2-dimethoxyl propane or a combination thereof.

In some embodiments, the dehydrating agent is in an amount of about 0.1-5 moles, relative to 1 mole of the alcohol compound.

In some embodiments, the synthesis reaction has a temperature in a range from about 80° C. to about 150° C. When the temperature is lower than 80° C., there is no reaction. If the temperature is higher than 150° C., the selectivity will decrease and the yield will also decrease.

In some embodiments, the synthesis reaction has a pressure in a range from about 0.5 MPa to about 10 MPa.

In some embodiments, the synthesis reaction has a reaction time which is in a range from about 4 hours to about 72 hours. When the reaction time is less than 4 hours, the yield is too low. If the reaction time exceeds 72 hours, the selectivity decreases, resulting in a decrease in yield.

In some embodiments, the synthesis reaction may be carried out in, for example, a batch reactor.

In some embodiments, the synthesis reaction may be carried out in a continuous reactor.

In some embodiments, the continuous reactor may include a fixed-bed reactor, a moving-bed reactor or a continuous stirred-tank reactor.

In the disclosed synthesis reaction of the dialkyl carbonate, the organic acid (such as formic acid, acetic acid, propionic acid, butyric acid, valeric acid or a combination thereof) is directly added as a reaction auxiliary. Since the organic acid can be sufficiently mixed with the reaction liquid without poor dispersion, the reaction efficiency of the catalyst (for example, cerium oxide ($CeO_2$), zirconium oxide ($ZrO_2$), titanium oxide ($TiO_2$), lanthanum oxide ($La_2O_3$) or a combination thereof) can be greatly improved, thereby increasing the yield of the dialkyl carbonate. In addition, in the above synthesis reaction, adding the dehydrating agent (including 2-cyanopyridine, alkali metal silicoaluminate (zeolite molecular sieves, such as 3A zeolite molecular sieves), benzonitrile, 2,2-dimethoxyl propane or a combination thereof) is more helpful to improving the yield of the dialkyl carbonate. Furthermore, in the reaction, by appropriately adjusting the weight ratio between the alcohol compound, the catalyst and the organic acid, and appropriately adjusting the reaction conditions such as reaction temperature and pressure, the yield of the dialkyl carbonate can be effectively improved.

EXAMPLES/COMPARATIVE EXAMPLES

Example 1

The Preparation of Dialkyl Carbonate (1) (Methanol/Cerium Oxide ($CeO_2$)/Acetic Acid)

16 g of methanol, 1 g of cerium oxide ($CeO_2$) and 0.3 g of acetic acid were placed in an autoclave. Carbon dioxide with the pressure of 4 MPa was conducted into the autoclave. At a temperature of 110° C., the cerium oxide ($CeO_2$) was used as a catalyst, and the stirring was continued to carry out the synthesis reaction. After the reaction proceeded for 24 hours, dimethyl carbonate (DMC) was directly obtained at a yield of 1.12%.

Example 2

The Preparation of Dialkyl Carbonate (2) (Methanol/Cerium Oxide ($CeO_2$)/Butyric Acid)

64 g of methanol, 6 g of cerium oxide ($CeO_2$) and 0.5 g of butyric acid were placed in an autoclave. Carbon dioxide with the pressure of 4 MPa was conducted into the autoclave. At a temperature of 110° C., the cerium oxide ($CeO_2$) was used as a catalyst, and the stirring was continued to carry out the synthesis reaction. After the reaction proceeded for 24 hours, dimethyl carbonate (DMC) was directly obtained at a yield of 1.07%.

Example 3

The Preparation of Dialkyl Carbonate (3) (Methanol/Zirconium Oxide ($ZrO_2$)/Acetic Acid)

64g of methanol, 6g of zirconium oxide ($ZrO_2$) and 0.3 g of acetic acid were placed in an autoclave. Carbon dioxide with the pressure of 4 MPa was conducted into the autoclave. At a temperature of 110° C., the zirconium oxide ($ZrO_2$) was used as a catalyst, and the stirring was continued to carry out the synthesis reaction. After the reaction proceeded for 24 hours, dimethyl carbonate (DMC) was directly obtained at a yield of 1.02%.

Example 4

The Preparation of Dialkyl Carbonate (4) (Methanol/Zirconium Oxide ($ZrO_2$)/Butyric Acid)

64g of methanol, 6g of zirconium oxide ($ZrO_2$) and 0.5 g of butyric acid were placed in an autoclave. Carbon dioxide with the pressure of 4 MPa was conducted into the autoclave. At a temperature of 110° C., the zirconium oxide ($ZrO_2$) was used as a catalyst, and the stirring was continued to carry out the synthesis reaction. After the reaction proceeded for 24 hours, dimethyl carbonate (DMC) was directly obtained at a yield of 0.94%.

Example 5

The Preparation of Dialkyl Carbonate (5) (Methanol/Cerium Oxide ($CeO_2$)/Zirconium Oxide ($ZrO_2$)/Acetic Acid)

64 g of methanol, 4.8 g of cerium oxide ($CeO_2$), 1.2 g of zirconium oxide ($ZrO_2$) and 0.3 g of acetic acid were placed in an autoclave. Carbon dioxide with the pressure of 4 MPa was conducted into the autoclave. At a temperature of 110° C., a combination of cerium oxide ($CeO_2$) and zirconium oxide ($ZrO_2$) was used as a catalyst, and the stirring was continued to carry out the synthesis reaction. After the reaction proceeded for 24 hours, dimethyl carbonate (DMC) was directly obtained at a yield of 1.30%.

Example 6

The Preparation of Dialkyl Carbonate (6) (Methanol/Cerium Oxide ($CeO_2$)/Zirconium Oxide ($ZrO_2$)/Butyric Acid)

64 g of methanol, 4.8 g of cerium oxide ($CeO_2$), 1.2 g of zirconium oxide ($ZrO_2$) and 0.5 g of butyric acid were placed in an autoclave. Carbon dioxide with the pressure of 4 MPa was conducted into the autoclave. At a temperature of 110° C., a combination of cerium oxide ($CeO_2$) and zirconium oxide ($ZrO_2$) was used as a catalyst, and the stirring was continued to carry out the synthesis reaction. After the reaction proceeded for 24 hours, dimethyl carbonate (DMC) was directly obtained at a yield of 1.08%.

Example 7

The Preparation of Dialkyl Carbonate (7) (Methanol/Cerium Oxide ($CeO_2$)/Acetic Acid/2-Cyanopyridine)

16 g of methanol, 2 g of cerium oxide ($CeO_2$), 0.15 g of acetic acid and 50 g of 2-cyanopyridine (dehydrating agent) were placed in an autoclave. Carbon dioxide with the pressure of 4 MPa was conducted into the autoclave. At a temperature of 110° C., the cerium oxide ($CeO_2$) was used as a catalyst, and the stirring was continued to carry out the synthesis reaction. After the reaction proceeded for 6 hours, dimethyl carbonate (DMC) was directly obtained at a yield of 68.06%.

Example 8

The Preparation of Dialkyl Carbonate (8) (Methanol/Cerium Oxide ($CeO_2$)/Butyric Zcid/2-Cyanopyridine)

64 g of methanol, 6 g of cerium oxide ($CeO_2$), 0.5 g of butyric acid and 110g of 2-cyanopyridine (dehydrating agent) were placed in an autoclave. Carbon dioxide with the pressure of 4 MPa was conducted into the autoclave. At a temperature of 110° C., the cerium oxide ($CeO_2$) was used as a catalyst, and the stirring was continued to carry out the synthesis reaction. After the reaction proceeded for 24 hours, dimethyl carbonate (DMC) was directly obtained at a yield of 66.86%.

Example 9

The Preparation of Dialkyl Carbonate (9) (Methanol/Cerium Oxide ($CeO_2$)/Acetic Acid/2,2-Dimethoxyl Propane)

100 g of methanol, 7 g of cerium oxide ($CeO_2$), 0.3 g of acetic acid and 20 g of 2,2-dimethoxyl propane (dehydrating agent) were placed in an autoclave. Carbon dioxide with the pressure of 4 MPa was conducted into the autoclave. At a temperature of 120° C., the cerium oxide ($CeO_2$) was used as a catalyst, and the stirring was continued to carry out the synthesis reaction. After the reaction proceeded for 24 hours, dimethyl carbonate (DMC) was directly obtained at a yield of 3.63%.

Example 10

The Preparation of Dialkyl Carbonate (10) (Methanol/Zirconium Oxide ($ZrO_2$)/Acetic Acid/2-Cyanopyridine)

64 g of methanol, 6 g of zirconium oxide ($ZrO_2$), 0.3 g of acetic acid and 100 g of 2-cyanopyridine (dehydrating agent) were placed in an autoclave. Carbon dioxide with the pressure of 4 MPa was conducted into the autoclave. At a temperature of 110° C., the zirconium oxide ($ZrO_2$) was used as a catalyst, and the stirring was continued to carry out the synthesis reaction. After the reaction proceeded for 24 hours, dimethyl carbonate (DMC) was directly obtained at a yield of 13.7%.

Example 11

The Preparation of Dialkyl Carbonate (11) (Methanol/Zirconium Oxide ($ZrO_2$)/Acetic Acid/2,2-Dimethoxyl Propane)

100 g of methanol, 7 g of zirconium oxide ($ZrO_2$), 0.3 g of acetic acid and 20 g of 2,2-dimethoxyl propane (dehydrating agent) were placed in an autoclave. Carbon dioxide with the pressure of 4 MPa was conducted into the autoclave. At a temperature of 120° C., the zirconium oxide ($ZrO_2$) was used as a catalyst, and the stirring was continued to carry out the synthesis reaction. After the reaction proceeded for 24 hours, dimethyl carbonate (DMC) was directly obtained at a yield of 2.87%.

Example 12

The Preparation of Dialkyl Carbonate (12) (Methanol/Cerium Oxide ($CeO_2$)/Zirconium Oxide ($ZrO_2$)/Acetic Acid/2-Cyanopyridine)

32 g of methanol, 0.8 g of cerium oxide ($CeO_2$), 0.2 g of zirconium oxide ($ZrO_2$), 0.3 g of acetic acid and 50 g of 2-cyanopyridine (dehydrating agent) were placed in an autoclave. Carbon dioxide with the pressure of 4M Pa was conducted into the autoclave. At a temperature of 110° C., a combination of cerium oxide ($CeO_2$) and zirconium oxide ($ZrO_2$) was used as a catalyst, and the stirring was continued to carry out the synthesis reaction. After the reaction proceeded for 24 hours, dimethyl carbonate (DMC) was directly obtained at a yield of 90.26%.

Example 13

The Preparation of Dialkyl Carbonate (13) (Methanol/Cerium oxide ($CeO_2$)/zirconium oxide ($ZrO_2$)/acetic acid/2,2-Dimethoxyl Propane)

32 g of methanol, 4.8 g of cerium oxide ($CeO_2$), 1.2 g of zirconium oxide ($ZrO_2$), 0.3 g of acetic acid and 20 g of 2,2-dimethoxyl propane (dehydrating agent) were placed in an autoclave. Carbon dioxide with the pressure of 4 MPa was conducted into the autoclave. At a temperature of 120° C., a combination of cerium oxide ($CeO_2$) and zirconium oxide ($ZrO_2$) was used as a catalyst, and the stirring was continued to carry out the synthesis reaction. After the reaction proceeded for 24 hours, dimethyl carbonate (DMC) was directly obtained at a yield of 3.47%.

Example 14

The Preparation of Dialkyl Carbonate (14) (Methanol/Cerium Oxide ($CeO_2$)/Zirconium Oxide ($ZrO_2$)/Valeric Acid)

64 g of methanol, 4.8 g of cerium oxide ($CeO_2$), 1.2 g of zirconium oxide ($ZrO_2$) and 0.6 g of valeric acid were placed in an autoclave. Carbon dioxide with the pressure of 4 MPa was conducted into the autoclave. At a temperature of 110° C., a combination of cerium oxide ($CeO_2$) and zirconium oxide ($ZrO_2$) was used as a catalyst, and the stirring was continued to carry out the synthesis reaction. After the reaction proceeded for 24 hours, dimethyl carbonate (DMC) was directly obtained at a yield of 0.92%.

Example 15

The Preparation of Dialkyl Carbonate (15) (Ethanol/Cerium Oxide ($CeO_2$)/Acetic Acid)

32 g of ethanol, 2 g of cerium oxide ($CeO_2$) and 0.3 g of acetic acid were placed in an autoclave. Carbon dioxide with the pressure of 4M Pa was conducted into the autoclave. At a temperature of 110° C., the cerium oxide ($CeO_2$) was used as a catalyst, and the stirring was continued to carry out the synthesis reaction. After the reaction proceeded for 24 hours, diethyl carbonate (DEC) was directly obtained at a yield of 0.27%.

Example 16

The Preparation of Dialkyl Carbonate (16) (Ethanol/Zirconium Oxide ($ZrO_2$)/Acetic Acid)

64 g of ethanol, 6 g of zirconium oxide ($ZrO_2$) and 0.3 g of acetic acid were placed in an autoclave. Carbon dioxide with the pressure of 4 MPa was conducted into the autoclave. At a temperature of 110° C., the zirconium oxide ($ZrO_2$) was used as a catalyst, and the stirring was continued to carry out the synthesis reaction. After the reaction proceeded for 24 hours, diethyl carbonate (DEC) was directly obtained at a yield of 0.12%.

Example 17

The Preparation of Dialkyl Carbonate (17) (Ethanol/Cerium Oxide ($CeO_2$)/Zirconium Oxide ($ZrO_2$)/Acetic Acid)

64 g of ethanol, 4.8 g of cerium oxide ($CeO_2$), 1.2 g of zirconium oxide ($ZrO_2$) and 0.3 g of acetic acid were placed in an autoclave. Carbon dioxide with the pressure of 4 MPa was conducted into the autoclave. At a temperature of 110° C., a combination of cerium oxide ($CeO_2$) and zirconium oxide ($ZrO_2$) was used as a catalyst, and the stirring was continued to carry out the synthesis reaction. After the reaction proceeded for 24 hours, diethyl carbonate (DEC) was directly obtained at a yield of 0.34%.

Example 18

The Preparation of Dialkyl Carbonate (18) (Propanol/Cerium Oxide ($CeO_2$)/Acetic Acid)

32 g of propanol, 2 g of cerium oxide ($CeO_2$) and 0.3 g of acetic acid were placed in an autoclave. Carbon dioxide with the pressure of 4 MPa was conducted into the autoclave. At a temperature of 110° C., the cerium oxide ($CeO_2$) was used as a catalyst, and the stirring was continued to carry out the synthesis reaction. After the reaction proceeded for 24 hours, dipropyl carbonate (DPC) was directly obtained at a yield of 0.03%.

Example 19

The Preparation of Dialkyl Carbonate (19) (Propanol/Zirconium Oxide ($ZrO_2$)/Acetic Acid)

32 g of propanol, 6 g of zirconium oxide ($ZrO_2$) and 0.3 g of acetic acid were placed in an autoclave. Carbon dioxide with the pressure of 4 MPa was conducted into the autoclave. At a temperature of 110° C., the zirconium oxide ($ZrO_2$) was used as a catalyst, and the stirring was continued to carry out the synthesis reaction. After the reaction proceeded for 24 hours, dipropyl carbonate (DPC) was directly obtained at a yield of 0.02%.

Example 20

The Preparation of Dialkyl Carbonate (20) (Propanol/Cerium Oxide ($CeO_2$)/Zirconium Oxide ($ZrO_2$)/Acetic Acid)

32 g of propanol, 4.8 g of cerium oxide ($CeO_2$), 1.2 g of zirconium oxide ($ZrO_2$) and 0.3 g of acetic acid were placed in an autoclave. Carbon dioxide with the pressure of 4 MPa was conducted into the autoclave. At a temperature of 110° C., a combination of cerium oxide ($CeO_2$) and zirconium oxide ($ZrO_2$) was used as a catalyst, and the stirring was continued to carry out the synthesis reaction. After the reaction proceeded for 24 hours, dipropyl carbonate (DPC) was directly obtained at a yield of 0.05%.

Comparative Example 1

The Preparation of Dialkyl Carbonate (1) (Methanol/Cerium Oxide ($CeO_2$))

16 g of methanol and 1 g of cerium oxide ($CeO_2$) were placed in an autoclave. Carbon dioxide with the pressure of 4 MPa was conducted into the autoclave. At a temperature of 110° C., the cerium oxide ($CeO_2$) was used as a catalyst, and the stirring was continued to carry out the synthesis reaction. After the reaction proceeded for 24 hours, dimethyl carbonate (DMC) was directly obtained at a yield of 0.92%.

Comparative Example 2

The Preparation of Dialkyl Carbonate (2) (Methanol/Zirconium Oxide ($ZrO_2$))

64 g of methanol and 6 g of zirconium oxide ($ZrO_2$) were placed in an autoclave. Carbon dioxide with the pressure of 4 MPa was conducted into the autoclave. At a temperature of 110° C., the zirconium oxide ($ZrO_2$) was used as a catalyst, and the stirring was continued to carry out the synthesis reaction. After the reaction proceeded for 24 hours, dimethyl carbonate (DMC) was directly obtained at a yield of 0.08%.

Comparative Example 3

The Preparation of Dialkyl Carbonate (3) (Methanol/Cerium Oxide ($CeO_2$)/zirconium oxide ($ZrO_2$))

16 g of methanol, 4.8 g of cerium oxide ($CeO_2$) and 1.2 g of zirconium oxide ($ZrO_2$) were placed in an autoclave. Carbon dioxide with the pressure of 4 MPa was conducted into the autoclave. At a temperature of 110° C., a combination of cerium oxide ($CeO_2$) and zirconium oxide ($ZrO_2$) was used as a catalyst, and the stirring was continued to carry out the synthesis reaction. After the reaction proceeded for 24 hours, dimethyl carbonate (DMC) was directly obtained at a yield of 0.07%.

Comparative Example 4

The Preparation of Dialkyl Carbonate (4) (Methanol/Cerium Oxide ($CeO_2$)/Sulfuric Acid)

32 g of methanol, 4 g of cerium oxide ($CeO_2$) and 0.3 g of sulfuric acid were placed in an autoclave. Carbon dioxide with the pressure of 5 MPa was conducted into the autoclave. At a temperature of 130° C., the cerium oxide ($CeO_2$) was used as a catalyst, and the stirring was continued to carry out the synthesis reaction. After the reaction proceeded for 24 hours, dimethyl carbonate (DMC) was directly obtained in a yield less than 0.01%.

Comparative Example 5

The Preparation of Dialkyl Carbonate (5) (Methanol/Zirconium Oxide ($ZrO_2$)/Sulfuric Acid)

32 g of methanol, 4 g of zirconium oxide ($ZrO_2$) and 0.3 g of sulfuric acid were placed in an autoclave. Carbon dioxide with the pressure of 5 MPa was conducted into the autoclave. At a temperature of 130° C., the zirconium oxide ($ZrO_2$) was used as a catalyst, and the stirring was continued to carry out the synthesis reaction. After the reaction proceeded for 24 hours, dimethyl carbonate (DMC) was directly obtained in a yield less than 0.01%.

Comparative Example 6

The Preparation of Dialkyl Carbonate (6) (Methanol/Cerium Oxide ($CeO_2$)/Zirconium Oxide ($ZrO_2$)/Sulfuric Acid)

32 g of methanol, 3.2 g of cerium oxide ($CeO_2$), 0.8 g of zirconium oxide ($ZrO_2$) and 0.3 g of sulfuric acid were placed in an autoclave. Carbon dioxide with the pressure of 5 MPa was conducted into the autoclave. At a temperature of 130° C., a combination of cerium oxide ($CeO_2$) and zirconium oxide ($ZrO_2$) was used as a catalyst, and the stirring was continued to carry out the synthesis reaction. After the reaction proceeded for 24 hours, dimethyl carbonate (DMC) was directly obtained in a yield less than 0.01%.

Comparative Example 7

The Preparation of Dialkyl Carbonate (7) (Methanol/Cerium Oxide ($CeO_2$)/Acetic Acid/the Parts by Weight of Cerium Oxide is Less than 0.5 (Relative to Methanol))

64 g of methanol, 0.2 g of cerium oxide ($CeO_2$) and 0.3 g of acetic acid were placed in an autoclave. Carbon dioxide with the pressure of 4 MPa was conducted into the autoclave. At a temperature of 110° C., the cerium oxide ($CeO_2$) was used as a catalyst, and the stirring was continued to carry out the synthesis reaction. After the reaction proceeded for 24 hours, dimethyl carbonate (DMC) was directly obtained at a yield of 0.05%.

Comparative Example 8

The Preparation of Dialkyl Carbonate (8) (Methanol/Cerium Oxide ($CeO_2$)/Zirconium Oxide ($ZrO_2$)/Acetic Acid/the Parts by Weight of Acetic Acid is Less than 0.01 (Relative to Methanol))

64 g of methanol, 4.8 g of cerium oxide ($CeO_2$), 1.2 g of zirconium oxide ($ZrO_2$) and 0.002 g of acetic acid were placed in an autoclave. Carbon dioxide with the pressure of 4 MPa was conducted into the autoclave. At a temperature of 110° C., a combination of cerium oxide ($CeO_2$) and zirconium oxide ($ZrO_2$) was used as a catalyst, and the stirring was continued to carry out the synthesis reaction. After the reaction proceeded for 24 hours, dimethyl carbonate (DMC) was directly obtained at a yield of 0.05%.

Comparative Example 9

The Preparation of Dialkyl Carbonate (9) (Methanol/Cerium Oxide ($CeO_2$)/Zirconium Oxide ($ZrO_2$)/Acetic Acid/the Parts by Weight of Acetic Acid is Greater than 2 (Relative to Methanol))

64 g of methanol, 4.8 g of cerium oxide ($CeO_2$), 1.2 g of zirconium oxide ($ZrO_2$) and 1.5 g of acetic acid were placed in an autoclave. Carbon dioxide with the pressure of 4 MPa was conducted into the autoclave. At a temperature of 110° C., a combination of cerium oxide ($CeO_2$) and zirconium oxide ($ZrO_2$) was used as a catalyst, and the stirring was continued to carry out the synthesis reaction. After the reaction proceeded for 24 hours, dimethyl carbonate (DMC) was directly obtained at a yield of 0.03%.

Comparative Example 10

The Preparation of Dialkyl Carbonate (10) (Methanol/Cerium Oxide ($CeO_2$)/Zirconium Oxide ($ZrO_2$)/Acetic Acid/the Reaction Temperature is Less than About 80° C.)

64 g of methanol, 4.8 g of cerium oxide ($CeO_2$), 1.2 g of zirconium oxide ($ZrO_2$) and 0.3 g of acetic acid were placed in an autoclave. Carbon dioxide with the pressure of 4 MPa was conducted into the autoclave. At a temperature of 60° C., a combination of cerium oxide ($CeO_2$) and zirconium oxide ($ZrO_2$) was used as a catalyst, and the stirring was continued. However, no reaction occurred.

Comparative Example 11

The Preparation of Dialkyl Carbonate (11) (Methanol/Cerium Oxide ($CeO_2$)/Zirconium Oxide ($ZrO_2$)/Acetic Acid/the Reaction Temperature is Greater than About 150° C.)

64 g of methanol, 4.8 g of cerium oxide ($CeO_2$), 1.2 g of zirconium oxide ($ZrO_2$) and 0.3 g of acetic acid were placed in an autoclave. Carbon dioxide with the pressure of 4 MPa was conducted into the autoclave. At a temperature of 170° C., a combination of cerium oxide ($CeO_2$) and zirconium oxide ($ZrO_2$) was used as a catalyst, and the stirring was continued to carry out the synthesis reaction. After the reaction proceeded for 24 hours, dimethyl carbonate (DMC) was directly obtained at a yield of 0.64%. However, many side reactions occurred.

Comparative Example 12

The Preparation of Dialkyl Carbonate (12) (Methanol/Cerium Oxide ($CeO_2$)/Zirconium Oxide ($ZrO_2$)/Acetic Acid/the Reaction Pressure is Less than About 0.5 MPa)

64 g of methanol, 4.8 g of cerium oxide ($CeO_2$), 1.2 g of zirconium oxide ($ZrO_2$) and 0.3 g of acetic acid were placed in an autoclave. Carbon dioxide with the pressure of 0.3 MPa was conducted into the autoclave. At a temperature of 110° C., a combination of cerium oxide ($CeO_2$) and zirconium oxide ($ZrO_2$) was used as a catalyst, and the stirring was continued. However, no reaction occurred.

Comparative Example 13

The Preparation of Dialkyl Carbonate (13) (Methanol/Cerium Oxide ($CeO_2$)/2-Cyanopyridine)

16 g of methanol, 2 g of cerium oxide ($CeO_2$) and 50 g of 2-cyanopyridine (dehydrating agent) were placed in an autoclave. Carbon dioxide with the pressure of 4 MPa was conducted into the autoclave. At a temperature of 110° C., the cerium oxide ($CeO_2$) was used as a catalyst, and the stirring was continued to carry out the synthesis reaction. After the reaction proceeded for 6 hours, dimethyl carbonate (DMC) was directly obtained at a yield of 32.35%.

In the disclosed synthesis reaction of the dialkyl carbonate, the organic acid (such as formic acid, acetic acid, propionic acid, butyric acid, valeric acid or a combination thereof) is directly added as a reaction auxiliary. Since the organic acid can be sufficiently mixed with the reaction liquid without poor dispersion, the reaction efficiency of the catalyst (for example, cerium oxide ($CeO_2$), zirconium oxide ($ZrO_2$), titanium oxide ($TiO_2$), lanthanum oxide ($La_2O_3$) or a combination thereof) can be greatly improved, thereby increasing the yield of the dialkyl carbonate. In addition, in the above synthesis reaction, adding the dehydrating agent (including 2-cyanopyridine, alkali metal silicoaluminate (zeolite molecular sieves, such as 3A zeolite molecular sieves), benzonitrile, 2,2-dimethoxyl propane or a combination thereof), is more helpful to improving the yield of the dialkyl carbonate. Furthermore, in the reaction, by appropriately adjusting the weight ratio between the alcohol compound, the catalyst and the organic acid, and appropriately adjusting the reaction conditions such as reaction temperature and pressure, the yield of the dialkyl carbonate can be effectively improved.

While the disclosure has been described by way of example and in terms of preferred embodiment, it should be understood that the disclosure is not limited thereto. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for preparing dialkyl carbonate, comprising:
   mixing methanol, carbon dioxide and a catalyst to form a mixing solution, wherein the catalyst comprises cerium oxide ($CeO_2$), zirconium oxide ($ZrO_2$), titanium oxide ($TiO_2$), lanthanum oxide ($La_2O_3$) or a combination thereof, and the catalyst is in an amount of 0.5-25 parts by weight, based on 100 parts by weight of the methanol; and
   adding organic acid to the mixing solution to carry out a synthesis reaction of dialkyl carbonate, wherein the organic acid comprises formic acid, acetic acid, propionic acid, butyric acid or a combination thereof.

2. The method for preparing dialkyl carbonate as claimed in claim 1, wherein the organic acid is in an amount of 0.01-2 parts by weight, based on 100 parts by weight of the methanol.

3. The method for preparing dialkyl carbonate as claimed in claim 1, further comprising adding a dehydrating agent to the mixing solution.

4. The method for preparing dialkyl carbonate as claimed in claim 3, wherein the dehydrating agent comprises 2-cyanopyridine, alkali metal silicoaluminate, benzonitrile, 2,2-dimethoxyl propane or a combination thereof.

5. The method for preparing dialkyl carbonate as claimed in claim 3, wherein the dehydrating agent is in an amount of 0.1-5 moles, relative to one mole of the methanol.

6. The method for preparing dialkyl carbonate as claimed in claim 1, wherein the synthesis reaction has a temperature in a range from 80° C. to 150° C.

7. The method for preparing dialkyl carbonate as claimed in claim 1, wherein the synthesis reaction has a pressure in a range from 0.5 MPa to 10 MPa.

8. The method for preparing dialkyl carbonate as claimed in claim 1, wherein the synthesis reaction has a reaction time which is in a range from 4 hours to 72 hours.

9. The method for preparing dialkyl carbonate as claimed in claim 1, wherein the synthesis reaction is carried out in a batch reactor.

10. The method for preparing dialkyl carbonate as claimed in claim 1, wherein the synthesis reaction is carried out in a continuous reactor.

11. The method for preparing dialkyl carbonate as claimed in claim 10, wherein the continuous reactor comprises a fixed-bed reactor, a moving-bed reactor or a continuous stirred-tank reactor.

\* \* \* \* \*